United States Patent [19]

Saffar

[11] Patent Number: 5,047,059
[45] Date of Patent: Sep. 10, 1991

[54] PROSTHESIS FOR METACARPOPEALANGEAL OR INTERPHALANGEAL ARTICULATION OF THE FINGERS

[76] Inventor: Philippe Saffar, 23 Boulevard d'Argenson, 92299 Neuilly-sur-Seine, France

[21] Appl. No.: 440,123

[22] Filed: Nov. 22, 1989

Related U.S. Application Data

[63] Continuation-in-part of Ser. No. 249,332, Sep. 26, 1988, abandoned.

[30] Foreign Application Priority Data

Sep. 28, 1987 [FR] France ............................... 87 13370

[51] Int. Cl.⁵ .............................................. A61F 2/42
[52] U.S. Cl. ........................................ 623/21; 623/18
[58] Field of Search ...................... 623/16, 18, 20, 21, 623/64

[56] References Cited

U.S. PATENT DOCUMENTS

| | | | |
|---|---|---|---|
| 3,506,982 | 4/1970 | Steffee | 623/21 |
| 3,694,821 | 10/1972 | Moritz | 623/20 |
| 3,990,118 | 1/1976 | Strickland et al. | 623/18 |
| 4,304,011 | 12/1981 | Whelan III | 623/21 |
| 4,865,606 | 9/1989 | Rehder | 623/20 |

FOREIGN PATENT DOCUMENTS

| | | | |
|---|---|---|---|
| 2417292 | 9/1979 | France | 623/21 |
| 840343 | 2/1984 | PCT Int'l Appl. | 623/18 |
| 2126097 | 3/1984 | United Kingdom | 623/64 |

Primary Examiner—Richard J. Apley
Assistant Examiner—Lynne A. Reichard
Attorney, Agent, or Firm—Breiner & Breiner

[57] ABSTRACT

Prosthesis made up of two components of which one is in the form of a cap comprising a dorsal part connecting two wings of which the palmar edges are asymmetrical on the dorsal side relative to the axis of the diaphysis. The second component comprises a head which fits into the cap and a collar having two concave cut-ins which cooperate with the edges of the cap during flexion. The palmar edges of the cap form a multicentric convex around which the second articulation component turns. In a preferred embodiment, the cap of the first component has a transverse pin affixed therein and the head of the second component has an open portion which provides the head with a hook-like form. The opening in the head acts in conjunction with the pin to prevent the accidental uncoupling of the two components when a postero-anterior force is placed on the prosthesis while simultaneously allowing for articulation of the prosthesis components.

13 Claims, 3 Drawing Sheets

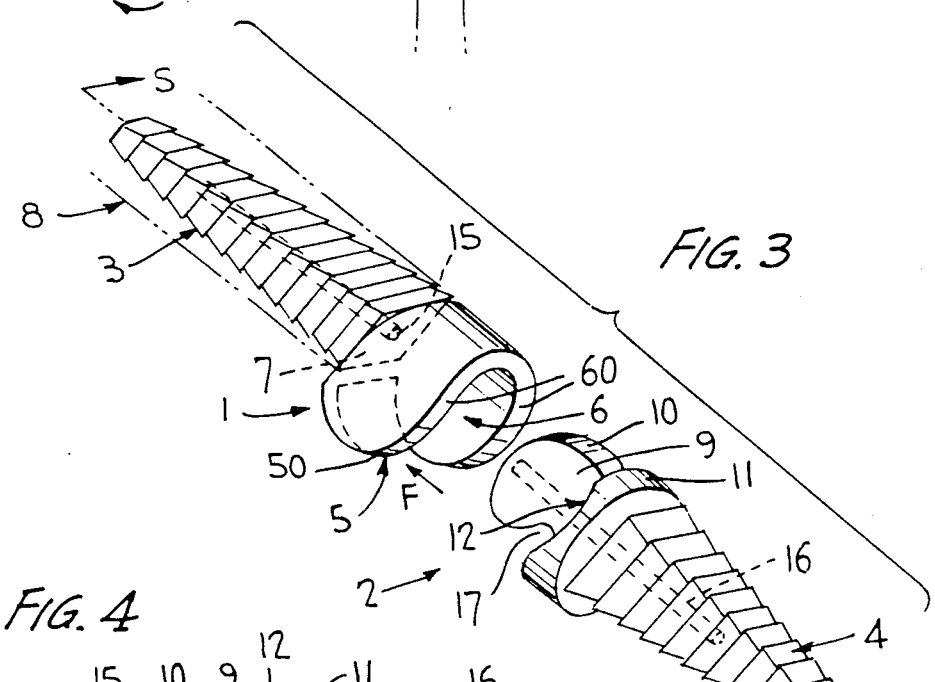

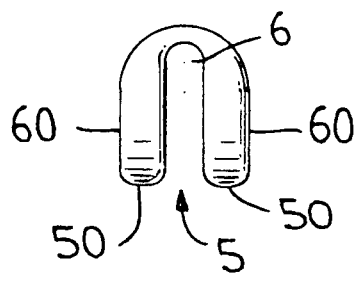
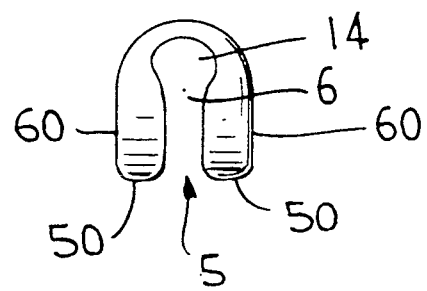
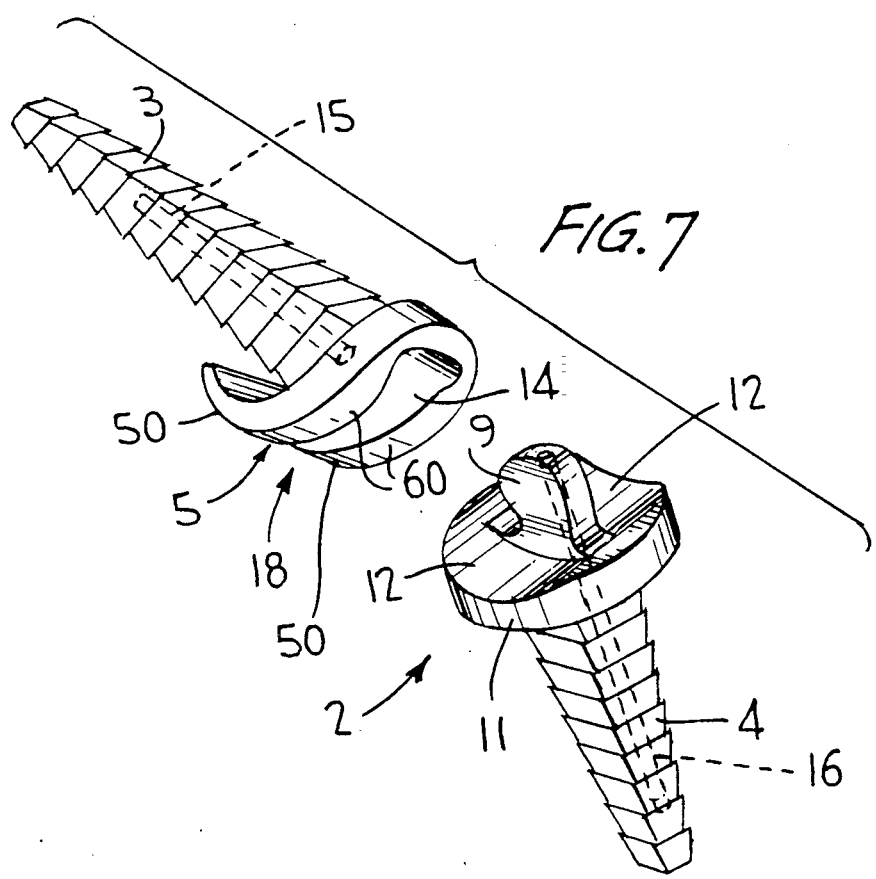

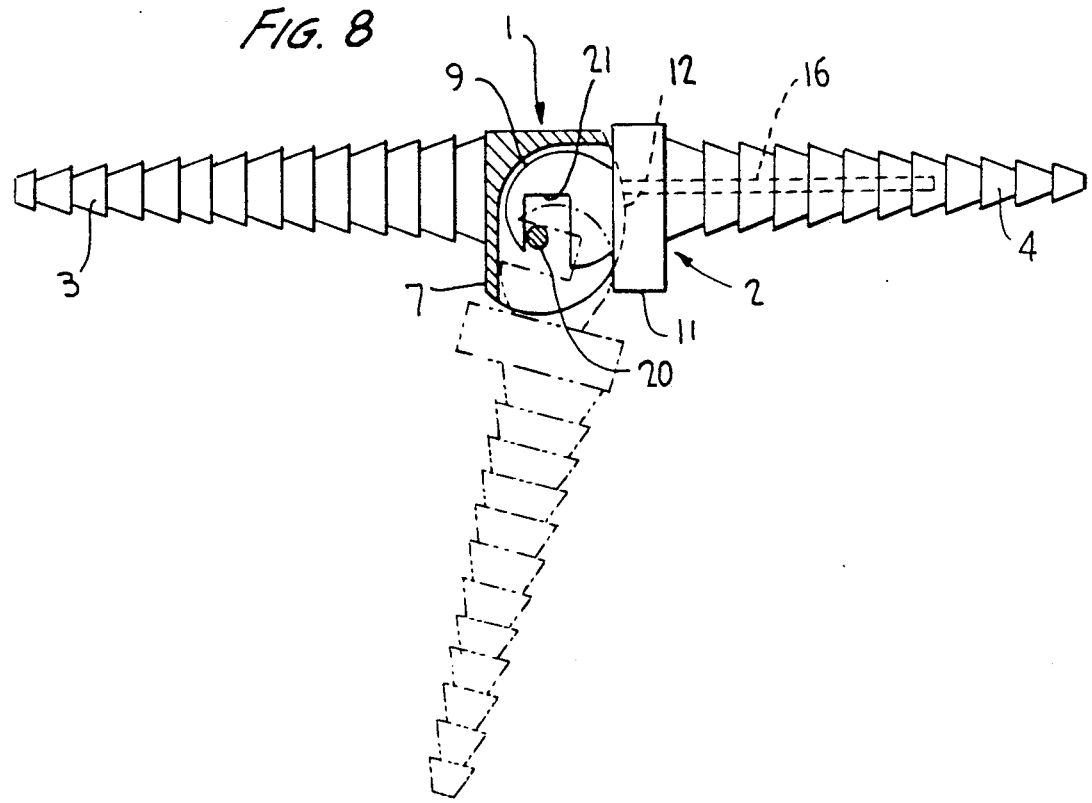
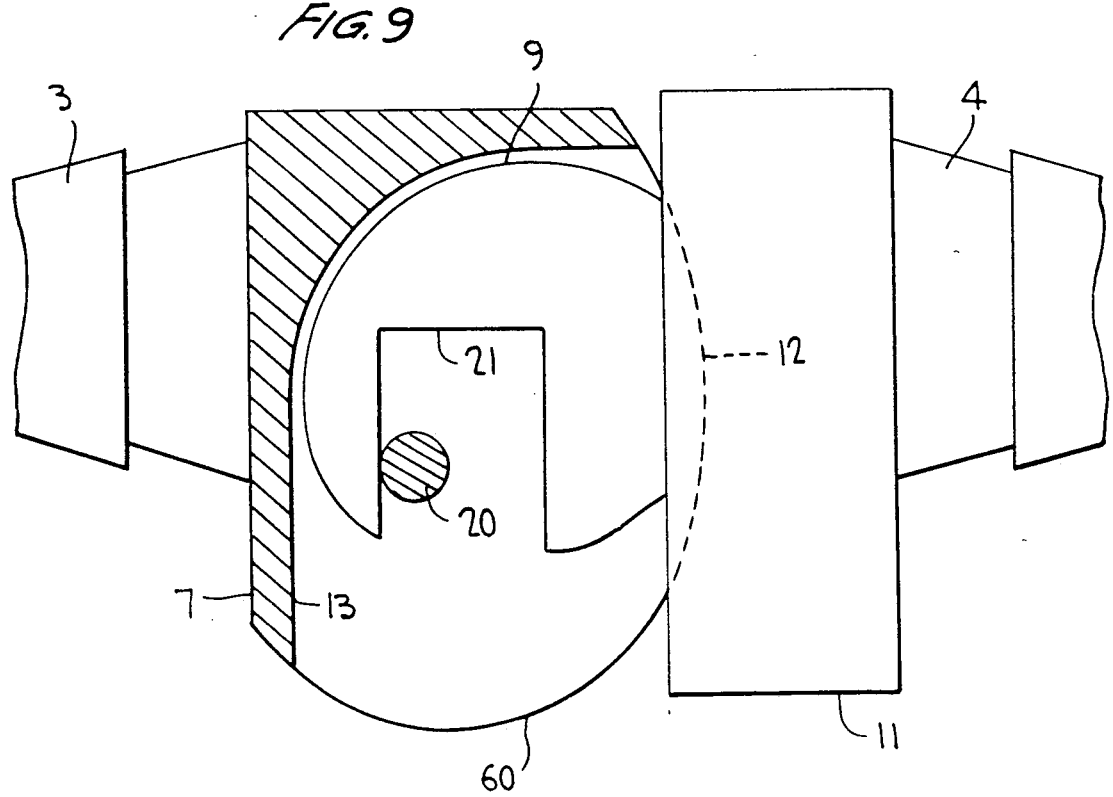

PROSTHESIS FOR METACARPOPEALANGEAL OR INTERPHALANGEAL ARTICULATION OF THE FINGERS

CROSS-REFERENCE TO RELATED APPLICATION

This application is a continuation-in-part of application Ser. No. 07/249,332, filed Sept. 26, 1988 now abandoned.

FIELD OF INVENTION

The invention relates to a prosthesis for finger joints and, more precisely, to a metacarpophalangeal or interphalangeal prosthesis made of two components constituting an actual joint. Each of the components is equipped with a stem which can be implanted in a medullary canal of a bone. One of the components affects the form of a socket which is open in the sagittal plane on the palmar side and in one of its adjacent sides which is opposite the adjacent side bearing the stem. The other joint component has a head capable of being accommodated in the socket and of turning against a concave portion provided in the bottom of the socket. The head is separated from the implant stem by a collar which is substantially perpendicular to the axis of the stem.

BACKGROUND OF THE INVENTION

The destruction of finger joints by a traumatism, degenerative or inflammatory rheumatism and, more rarely, an infection, creates a serious handicap which has been attempted to be overcome by implantation of metacarpophalangeal or interphalangeal prostheses.

For example, French Patent 2,242,067 describes a prosthesis made up of a piece of flexible material having transversely, in its middle, a thinned part which forms a flexible hinge. The ends of the piece constitute implant tails which are forced into the medullary canals.

Such prostheses allow a certain mobility to be recovered, but nevertheless impose a limitation on the mobility of the joint. In addition, numerous cases have been observed of osseous reactions around the prosthesis stems as a result of the wearing of the material and the emission of foreign bodies into the bone. The least serious disadvantage, which results from the repeated sliding of the stem in the medullary canal, is the possible enlargement of the latter.

French Patent 2,450,600 avoided this disadvantage by providing, on the joint components, pins capable of sliding freely in bushings formed in pads embedded in the medullary canals. The joint is thus held in place solely by the ligaments and tendons. The joint is made up of a head of cylindrical form mounted on the pin which slides in one of the medullary end pieces. The head cooperates with the concave surface of a plastic stem accommodated in a socket mounted on the pin sliding in the other end piece. The joint axis is the longitudinal axis of the cylindrical head. In order to achieve a certain degree of freedom in the radio-cubital plane of the articulation, the ends of the cylindrical head are hemispherical. The joint is held and returned by the natural ligaments and tendons.

In the hinge prosthesis, there are losses in extension and flexion due to the fact that the extensor and flexor tendons cannot ensure their function of adapting to the variable length of the fingers between the extension and flexion positions.

More particularly, if the length of the dorsal face of a finger is measured, it is found that the finger is shorter in extension than in flexion. This difference is explained by the fact that the phalanges in the flexion position put themselves one in front of the other (FIG. 1) and do not turn about a single axis. To each angle of flexion there corresponds an axis of rotation. The distal part of the metacarpals and also of the phalanges has, in the sagittal plane, a head which is asymmetrical relative to the axis of the metacarpal or phalanx projecting in the palmar direction.

The compensation mechanisms existing in the flexor tendons and the extensor tendons make it possible to redress the differences in length, for example, by bringing closer together or distancing the small lateral ligaments of the extensors in extension and in flexion (FIGS. 2A and 2B).

OBJECT AND BRIEF SUMMARY OF THE INVENTION

The invention aims to provide a multiaxial joint corresponding to the physiology of normal joints.

The prosthesis according to the invention is remarkable in that the socket forms a cap comprising a dorsal side capable of extending a part of the diaphysis and connecting two wings which are parallel to the sagittal plane passing through the principal plane of symmetry of the cap. The palmar edges of the wings are asymmetrical on the dorsal side of the cap relative to the axis of the diaphysis and project relative to the palmar part of the diaphysis to form a convex curve connected in a continuous curve to the adjacent edges, which are also of convex form, to form a multicentric curve. The joint component also comprises a head whose plane of symmetry corresponds to the sagittal plane. The head is separated from the implant tail or stem by a collar positioned perpendicular to the axis of the stem. Positioned in the collar, on either side of the head and parallel to the sagittal plane, are concave cut-ins whose curvature corresponds substantially to the curvature of the edges of the cap which face the collar when the prosthesis is in the extension position. The cut-ins also cooperate with the edges of the cap during flexion. A combined pin/hook system when associated with the engaged head and socket prevents accidental dislocation of the prosthesis while permitting the coupling or uncoupling of the head and socket during a surgical operation.

The description and figures given hereinafter by way of example will permit an understanding of how the invention can be achieved.

BRIEF DESCRIPTION OF DRAWINGS

FIG. 1 is a view, in the sagittal plane, of the interphalangeal joints when flexed.

FIGS. 2A and 2B show the position of the central slip of the extensor tendon in the compensation mechanism, the phalanges being extended and flexed respectively.

FIG. 3 is a perspective and exploded view of one embodiment of a prosthesis according to the invention.

FIG. 4 is a partial cutaway view of the prosthesis of FIG. 3 in extension (full lines) and in flexion (broken lines).

FIG. 5 is a view according to F in FIG. 3.

FIG. 6 is a view according to F in FIG. 3 of another embodiment.

FIG. 7 is an exploded perspective view of another embodiment of the prosthesis according to the invention.

FIG. 8 is a partial cutaway view of another alternative embodiment of the prosthesis of the present invention.

FIG. 9 is a partial cutaway view of the pin and hook arrangement of the embodiment shown in FIG. 8.

DESCRIPTION OF PRESENTLY PREFERRED EMBODIMENT

This prosthesis is intended for the replacement of the metacarpophalangeal and interphalangeal joints after resection of the distal and proximal articular osseous parts and preparation of the diaphyses.

The prosthesis is made up of two components 1 and 2 equipped with embedding stems 3 and 4 which are intended to be implanted in the medullary canals of the bones.

Joint component 1 is in the form of a socket forming a cap whose principal plane of symmetry is the sagittal plane S. The socket is open in this same plane on the palmar side 5 and one side 6 which is one of the sides adjacent to the palmar side. Side 7, the other side adjacent to the palmar side, bears perpendicularly on its face to embedding stem 3.

According to the embodiment shown in FIGS. 3, 5 and 6, the dorsal side of the socket-cap is substantially cylindrical in form and has an axis substantially parallel to the axis of the stem and, in cross-section, has a curvature which corresponds approximately to that of diaphyses 8 from which it extends.

The edges 50 on the palmar side 5 of the wings of the cap are parallel to the sagittal plane and are asymmetrical on the dorsal side of the cap relative to the axis of the implant stem corresponding substantially to the axis of the metacarpal or phalangeal diaphyses. Edges 50 form, in the sagittal plane, a convex curve which is connected in a continuous curve to likewise convex edges 60 of side 6 of the cap. The convex curve formed by sides 5 and 6 does not have a single center of curvature.

The curvature of the edges is designed so that the longitudinal displacement of the phalanx from the extension position to the flexion position is comparable to the displacement which is effected in the physiological articulation. This is achieved by the cap having a height greater than its length, with the length being determined according to the axis of the implant stem and with the height, which is perpendicular to the length, determined at the highest part at the top of the convexity of edges 50.

In the exemplary embodiments shown, the socket cap, which is preferably fixed on the metacarpal for the metacarpophalangeal prostheses and on the first phalanx for the proximal interphalangeal articulations, will be referred to by the term "proximal piece", while joint component 2 will be referred to by the term "distal piece".

Joint component or distal piece 2 comprises a head 9 whose plane of symmetry corresponds to the sagittal plane. The dimensions of the head are such that its width corresponds approximately to the smallest internal width between the parallel sides of cap 1 and its length is such that dorsal part 10 is in contact with the bottom of the cap when in the extension position.

The head is separated from implant stem 4 by a collar 11 which is positioned perpendicular to the axis of the stem. On either side of the head, parallel to the sagittal plane, concave cut-ins 12 are present in the collar. The curvature of cut-ins 12 correspond substantially to the curvature of the part of edges 60 of proximal piece 1 which face the collar 11 in the extension position. These cut-ins, as well as the form of the head, prevent rotation and lateral movements.

According to the embodiments shown, the end of the head has a convex cam profile provided for cooperating with a slide track 13 which is formed inside the cap on the dorsal side and on part 7 which bears on implant stem 3. While the distal piece slides along the edge of the cap of the proximal piece, contact is maintained, on the one hand, between the cam-profile head 9 and slide track 13 and, on the other hand, between the concave cut-ins 12 of collar 11 and convex edges 50 and 60 of the cap. The sagittal sides of the cap prevent lateral movements and replace the lateral ligaments (FIG. 5).

According to an embodiment more particularly adapted for metacarpophalangeal articulations having lateral movements in extension, a widening 14 (FIG. 6) is formed in the upper part near the bottom of the cap. This widening permits the distal piece to execute moderate lateral movements corresponding to the physiological movements. This widening can be combined with a loose complementary shaping of head 9 to prevent an uncoupling of the assembled proximal and distal pieces 1 and 2.

According to the embodiment shown in FIGS. 3 and 4, the implant stems 3 and 4 are pyramidal with a rectangular base. The rectangular section of the stems is provided to allow penetration into the oval-shaped medullary canals of the metacarpals and phalanges. The spaces existing between the surfaces of the tails and the medullary canal permit new bone growth to ensure the support of the prosthesis.

According to one embodiment, the tails are made of polyethylene strengthened axially over at least a part of their length by a metallic rod 15 and 16.

The cap is made of a physiologically compatible metal such as, for example, titanium. Where appropriate, the cap can have a coating of ceramic material on its dorsal part. The strengthening rod 15 is then also of titanium and is fixed in the metallic wall 7 of the cap.

The distal piece comprising the head, collar and stem is made of polyethylene strengthened axially over at least a part of its length by a metallic rod. The rod is preferably flush with the end of the head, where it forms a cam profile surface for sliding on the slide track of the cap.

Limiting the length of the rod to about half the length of the stems permits adjustment of the length of the stems to the depth of the prepared part of the medullary canal by simply cutting away the excess part of polyethylene.

The purpose of the strengthening rod is to avoid breaking of the cap or the head from the implant tail during the positioning or removal of the proximal and distal parts. Where appropriate, the strengthening rod and the tail are made integral by a pin passing through them in such a manner as to prevent any rotation between the two pieces.

The palmar side of head 9 has a notch 17 formed therein which makes it possible to increase the angle of flexion (FIG. 4) of the distal piece before it abuts against the side 7 of the cap.

According to a second exemplary embodiment as shown in FIG. 7, the cap is replaced by a shield 18 whose curved surface corresponds to the edges of convex form 50 and 60 of the cap in the preceding example. This embodiment is used when the palmar plate of the joint is in good condition and can be preserved. In this new embodiment the components similar to those of the first example have the same references.

FIGS. 8 and 9 illustrate another alternative embodiment which is a modified version of the prosthesis shown in FIGS. 3 and 4. FIGS. 8 and 9 utilize the same reference numbers as used in FIGS. 3 and 4 to denote parts in common. The modification to the prosthesis is in the socket or cap 1 of the proximal piece and head 9 of the distal piece.

The modification to the socket structure involves the inclusion of a transverse pin 20 within the socket of the proximal piece. Head 9 is modified by utilizing an opening or recess 21 in the head to provide a hook-like structure to the head of the distal piece. The transverse pin/hook system is an anti-luxation means for preventing the accidental uncoupling of the distal and proximal components. To a certain extent, the purpose of the pin/hook system is comparable to that of the loose complementary shaping of head 9 in the upper portion 14 of the socket as shown in FIG. 6. The embodiment shown in FIG. 6 permits moderate lateral movement of the distal piece in a metacarpophalangeal joint and prevents the uncoupling of the joint components.

More specifically, with reference to FIGS. 8 and 9, a transverse pin 20 is fixed in socket 1 of the proximal component and head 9 is structured in the form of a hook through the presence of opening 21 in head 9. According to a preferred embodiment, socket 1 is made integral with stem 3 from a physiologically compatible metal such as, for example, titanium. Similarly, head 9 is preferably made integral with stem 4, from polyethylene for example, and strengthened axially by a metal rod 16. The hook is positioned around and engages pin 20 to prevent an anterior dislocation of the prosthesis when a postero-anterior force is exerted on the distal component. A postero-anterior force, as denoted by the arrow in FIG. 8, is directed from the dorsal side towards the palmar side of the joint. In the absence of pin 20, such a force oriented perpendicularly to the stem axis of distal component 4, will disengage the distal component from socket 1 causing dislocation of the prosthesis. The extensor tendons alone are ineffective to prevent such a dislocation by a postero-anterior force.

Pin 20 is affixed transversely in socket 1 to and between the parallel wings of the socket in such a manner that the hook portion 21 of head 9 can be positioned around pin 20. The exterior surfaces of the head cam along the interior surface of the socket in the same manner as described above in reference to the embodiment shown in FIGS. 3 and 4 due to the convex cam profile of head 9 and slide track 13 of socket 1.

When the distal component is in a position as shown by the dashed lines in FIG. 8, the distal component can be either coupled or uncoupled from the proximal component during a surgical operation.

When the pin/hook system is incorporated in the components of a prosthesis having a socket sized so that its height is larger than its length, the hook is structured so that its width accommodates the variations in the distance between pin 20 and socket edges 60 so that edges 60 will remain in camming contact with collar 11 as described with respect to the embodiment shown in FIGS. 3 and 4.

Pin 20 does not define a rotation axis for the distal component. Relative movements of both the proximal and distal components are assisted and adjusted by the above-described camming surfaces of socket edges 60 and concave cut-ins 12 of collar 11 which are resiliently urged against each other by the extensor tendons. Camming surface 13 also acts in conjunction with head 9 in promoting the camming interaction of socket edges 60 and concave cut-ins 12 of collar 11. Pin 20 acts in conjunction with opening 21 of head 9 to prevent dislocation of the prosthesis components while allowing for the physiological articulation of the components. Accordingly, the prosthesis components are provided with a means for limiting the motion of the prosthesis components using a rigid structure to prevent accidental dislocation or separation of the joint components while simultaneously permitting the flexible movement of the components necessary for normal physiological articulation.

The technique for positioning the metacarpophalangeal prostheses is known and is effected either by the dorsal approach or by the anterior approach.

The anterior approach is recommended in rheumatoid polyarthritis or if a significant attack of the palmar plate is suspected by anterior subluxation of the joint.

The positioning of the interphalangeal prostheses will be carried out dorsally by elevating a triangular flap, which is based distally, of the extensor apparatus containing the central band of the extensor tendon.

As will be apparent to one skilled in the art, various modifications can be made within the scope of the aforesaid description. Such modifications being within the ability of one skilled in the art form a part of the present invention and are embraced by the appended claims.

It is claimed:

1. A metacarpophalangeal or interphalangeal prosthesis comprising a proximal component and a distal component with each having a first end and a second end, with said second ends being joined together so that said components constitute a bone-like joint; each of said first ends of said proximal component and said distal component being a stem constructed and arranged for implantation into a medullary canal of a bone; said second end of said proximal component being a socket containing an opening, said opening being present on the palmar side and in a side of said socket in the sagittal plane not attached to said stem; and said second end of said distal component being a head constructed and arranged for insertion into said socket, said head being rotatable in said socket substantially in said sagittal plane in such a manner that each of said proximal and distal components are movable relative to each other between an extended position wherein said components are substantially aligned and a predetermined angular position on said palmar side, wherein the improvement comprises a pin fixed inside said socket transverse to said sagittal plane, and said head being in the form of a hook, with said hook being positioned around said pin in such a manner as to (a) prevent said proximal and said distal components from being unjoined when said distal component is subjected to a postero-anterior force which is substantially perpendicular to the axis of said stem of said distal component, and (b) allowing joining or unjoining of said second ends of said proximal and distal components by moving said distal component to a position on said palmar side which is substantially perpendicular to the axis of said stem of said proximal component.

2. A prosthesis according to claim 1 wherein said socket has edges along said opening in said sagittal plane which form a multicentric curved surface, and said head has a collar positioned between said head and said stem, said collar having concave cut-ins in the area surrounding said head which complement and cooperate with said multicentric curved surface during extension and flexion of said prosthesis components.

3. The prosthesis according to claim 1, wherein said head of said distal component has a convex cam profile and said socket has a slide track formed along an inside wall in such a manner that said slide track cooperates with said convex cam profile of said head during flexion of said prosthesis components.

4. The prosthesis according to claim 1 wherein said stems of said proximal and distal components are pyramidal in shape with a rectangular base.

5. The prosthesis according to claim 4 wherein said stems are composed of polyethylene.

6. The prosthesis according to claim 5 wherein said stems have a metallic strengthening rod inserted therein along at least a portion of said stems' longitudinal axis.

7. The prosthesis according to claim 6 wherein said strengthening rod of said proximal component is fixed at one end to said socket.

8. The prosthesis according to claim 6 wherein said strengthening rod of said distal component passes through said head.

9. The prosthesis according to claim 1 wherein said socket has a width which permits lateral movements of said head therein during extension of said proximal and distal components.

10. The prosthesis according to claim 1 wherein said socket is integral with said stem of said socket's first end.

11. The prosthesis according to claim 1 wherein said socket has a height larger than said socket's axial length.

12. The prosthesis according to claim 2 wherein said socket has a height larger than said socket's axial length.

13. The prosthesis according to claim 3 wherein socket has a height larger than said socket's axial length.

* * * * *